United States Patent [19]
Schalk et al.

[11] Patent Number: 5,601,745
[45] Date of Patent: Feb. 11, 1997

[54] MICROWAVE OVEN WITH TEMPERATURE AND PRESSURE MEASURING DEVICE

[75] Inventors: Andreas Schalk; Peter Kettisch; Helmut Sinabell, all of Graz; Johannes Zach, Marein, all of Austria

[73] Assignee: Anton Paar KG, Graz-Strassgang, Austria

[21] Appl. No.: 421,158

[22] Filed: Apr. 10, 1995

[30] Foreign Application Priority Data

Apr. 18, 1994 [DE] Germany .......................... 44 13 426.6

[51] Int. Cl.⁶ ..................................................... H05B 6/68
[52] U.S. Cl. ......................... 219/710; 219/686; 219/705; 422/21; 374/149
[58] Field of Search ................................. 219/710, 711, 219/713, 686, 704, 705; 422/21; 374/120, 121, 122, 123, 130, 149

[56] References Cited

U.S. PATENT DOCUMENTS

| | | |
|---|---|---|
| 2,943,605 | 7/1960 | Broders . |
| 3,100,997 | 8/1963 | Lorenz . |
| 4,088,863 | 5/1978 | Jellies ..................... 219/713 |
| 4,248,831 | 2/1981 | Hughes . |
| 4,401,625 | 8/1983 | Willay et al. . |
| 4,870,235 | 9/1989 | Steers et al. ............... 219/711 |
| 5,108,701 | 4/1992 | Zakaria et al. ............. 219/686 |
| 5,230,865 | 7/1993 | Hargett et al. . |
| 5,264,185 | 11/1993 | Floyd . |
| 5,403,564 | 4/1995 | Katschnig et al. ........... 422/21 |
| 5,430,275 | 7/1995 | Braunisch ................... 219/708 |
| 5,459,302 | 10/1995 | Jacqualt ..................... 219/711 |

FOREIGN PATENT DOCUMENTS

| | | |
|---|---|---|
| 2618969 | 11/1977 | Germany . |
| 3141939 | 5/1983 | Germany . |
| 299400 | 10/1983 | Germany . |
| 3600090 | 7/1987 | Germany . |
| 3620381 | 1/1988 | Germany . |
| 3919601 | 12/1989 | Germany . |
| 3818697 | 12/1989 | Germany ..................... 219/686 |
| 4114525 | 8/1992 | Germany . |
| 4108766 | 9/1992 | Germany . |
| 4300957 | 7/1994 | Germany . |
| 9406553 | 3/1994 | WIPO . |

OTHER PUBLICATIONS

Kojima et al., "Microwave digestion of biological samples with acid mixture in a closed double PTFE vessel for metal determination by one-drop flame atomic absorption spectrometry," *Analytica Chimica Acta*, 264:101–106, 1992.

Kojima et al, "Vapour–phase acid decomposition of high pure silicas in a sealed PTFE bomb and determination of impurities by one-drop atomic spectrometry," *Analytica Chimica Acta*, 245:35–41, 1991.

Buback, "Spektroskopie an fluiden Phasen–das Studium chemischer Reaktionen und Gleichgewichte bis zu hohem Druck," *Angew. Chem.*, 103:658–670, 1991.

Matusiewicz, "Development of a High Pressure/Temperature Focused Microwave Heated Teflon Bomb for Sample Preparation," *Anal. Chem.*, 66:751–755, 1994.

Lopez–Avila et al., "Microwave–Assisted Extraction of Organic Compounds from Standard Reference Soils and Sediments," *Anal. Chem.*, 66:1097–1106, 1994.

*Primary Examiner*—Philip H. Leung
*Attorney, Agent, or Firm*—Rothwell, Figg, Ernst & Kurz

[57] ABSTRACT

The present invention concerns a device for measuring the pressure and temperature in at least one pressure-tight analysis vessel, that has been sealed by means of a lid, whereby heat is supplied to the analysis vessel by means of a microwave oven. The device comprises a measurement device that is connected to a unit for controlling the microwave oven. In this regard, the measurement device is arranged in a microwave-tight housing inside the microwave field that is produced by the microwave oven. The housing is constructed in such a way that it forms a shield that is impermeable for the microwave field. A microwave-free zone is produced inside the housing. Electronic, current-carrying components can be arranged in the microwave-tight housing without, as a result, generating interference in the microwave field.

11 Claims, 2 Drawing Sheets

MICROWAVE OVEN WITH TEMPERATURE AND PRESSURE MEASURING DEVICE

BACKGROUND OF THE INVENTION

1. Field of the Invention

The present invention concerns a device for measuring the pressure and temperature in at least one pressure-tight analysis vessel, that has been sealed with a lid, whereby heat is supplied to the analysis vessel by means of a microwave oven and whereby the device comprises a measurement device that is connected to the microwave oven.

2. Description of the Background Art

A main task of chemical analysis comprises the determination of the composition of an unknown sample material. Thus, by way of example, the molecular formula of a chemical compound is determined in an elemental analysis. In various analysis procedures, especially elemental analysis, it is necessary, in an initial working step, to decompose the substance, that is to be investigated, either completely or partially, into the smallest element-specific molecules or ions. In the case of so-called acidic analysis, this degradation process is carried out with the help of one or more acids, oxidizing agents or other aggressive chemical substances. The fragments that are produced can be determined quantitatively and qualitatively in analysis steps that follow on therefrom. In acidic analysis, it is known that the yield can be significantly improved and the reaction time for the degradation of the substance can be drastically reduced by using high pressures and high temperatures. Thus, in addition to open analysis, analysis is frequently carried out under conditions of increased pressure and temperature. In order to reach the reaction temperatures, use is made of heating apparatus that, for example, utilize thermal radiation, thermal conduction or microwave energy.

The closed analysis vessels cannot withstand any arbitrarily high pressure and, as a rule, they are therefore equipped with a safety valve. The safety valve opens if the internal pressure exceeds a prescribed limiting value in the analysis vessel. During the opening of the safety valve, a portion of the substances, that are contained in the analysis vessel, escapes. An analysis vessel is described in DE 39 19 601 whose internal pressure acts on a pressure recorder that is connected to a control unit for the heating apparatus. As a result, one ensures that the heating apparatus is switched off before the upper pressure limit is reached.

If use is made of several analysis vessels with a communal heating apparatus, then the problem presents itself of monitoring the upper pressure limit for each individual vessel since different pressures arise in the individual analysis vessels especially as a result of exothermic reactions.

In German patent specification DE-OS 38 18 697, an attempt is made to solve the problem by using an individual reference vessel for the measurement of pressure. In the case of different pressures in the analysis vessels, the situation can arise that some of the analysis vessels release their pressure via a safety valve before the upper pressure limit has been reached in the reference vessel and this leads to the switching off of the heating apparatus.

This leads to losses of the sample. In the same way, the situation can also arise whereby the upper pressure limit is reached in the reference vessel and the heating apparatus is switched off before the required reaction temperature has been reached in the other vessels.

If microwave energy is used for heating, then a significant problem resides in the feature that the electrical lines that are used in, for example, transferring the measurements from the pressure recorder to the control unit for the heating apparatus are capable of absorbing microwave energy or causing interference in a microwave field. This has particularly disadvantageous effects if several analysis vessels are used simultaneously. The microwave field that is used for heating several analysis vessels is then no longer uniform and different amounts of heat are supplied to the individual analysis vessels. Although it is possible to shield the electrical lines with respect to the microwave field, this procedure is nevertheless time-consuming and costly. In addition, resonance positions in the microwave field can generate flash-over phenomena at the connections of the electrical lines.

SUMMARY OF THE INVENTION

The task of the present invention is to provide a device by means of which the pressure and the temperature can be measured in at least one heated, pressure-tight analysis vessel. In this connection, no interference in the microwave field, that is used to heat the sample, should be produced by the device itself, its energy supply or the transfer of measurements to a control unit.

This task is accomplished by a device for measuring the pressure and temperature in at least one pressure-tight analysis vessel, that is sealed by means of a lid, whereby heat is supplied to the analysis vessel by means of a microwave oven and whereby the device comprises a measurement device that is connected to a control unit for the microwave oven. In this regard, the measurement device is arranged inside the microwave field, that is produced by the microwave oven, in a microwave-tight housing. The housing is constructed in such a way that it forms a screen that is impermeable for the microwave field. A microwave-free zone is produced inside the housing. Electronic, current-conducting components can be arranged in the microwave-tight housing without, as a result, causing any interference in the microwave field.

The measurement device is connected to measurement sensors, that are arranged on the analysis vessel, by means of non-electrical lines. In addition, it is advantageous if the measurement device is connected to the control unit for the heating apparatus via a non-electrical line, whereby this has been arranged outside of the microwave field that is produced by the microwave oven. As a result of this arrangement, one ensures that no irregularities are generated in the microwave field that is used to heat the analysis vessels.

However, the measurement device can also be connected, via electrical lines, to measurement sensors, that have been arranged on the analysis vessel, provided that the electrical lines have been shielded with respect to the microwave field.

A measurement recorder is advantageously arranged in the microwave-tight housing, whereby the measurement recorder transforms the measurement signals from the measurement sensors into an electronic signal.

An energy source for the measurement device is advantageously arranged in the closed microwave-tight housing. A battery, an accumulator or a condenser with a high capacity can serve as a source of energy. This arrangement has the advantage that no electrical lines are required for the supply of energy to the measurement device.

The measurement device is advantageously connected, via a non-electrical line, to a source of energy outside of the closed microwave-tight housing. Interference with the microwave field is avoided as a result of the use of non-electrical lines for the supply of energy. One can, for example, arrange solar cells in the microwave-tight housing, whereby the solar cells are supplied with light energy from outside of the housing.

An energy converter is advantageously arranged in the closed microwave-tight housing for the conversion of microwave energy into electrical energy. In this way, a microwave-permeable zone is provided in the otherwise microwave-tight housing, whereby microwave energy can reach the energy converter through the microwave-permeable region. In this way, the microwave energy that is required for heating the analysis vessels can also be used to operate the measurement device.

A generator is advantageously arranged in the closed microwave-tight housing, whereby the generator is driven mechanically from outside of the housing.

A light transmitter is advantageously arranged in the measurement device, whereby the light transmitter serves in the opto-electrical transfer of the measurements to a receiver that is arranged outside of the measurement device and whereby the receiver is connected to the control unit for the heating apparatus. In this way, the measurements can be transferred to the control unit in a non-electrical manner without causing interference in the microwave field.

The transmitter and the receiver are advantageously connected via a light conductor.

The measurement sensors, that are arranged on the analysis vessel, are advantageously connected hydraulically, optically or thermally to the measurement device.

The measurement sensors, that are arranged on the analysis vessel, are advantageously connected to the measurement device by means of electrical lines that have been shielded off with respect to microwaves.

The device advantageously comprises two flanges that are held together by means of centro-symmetrically arranged bolt/nut connections and between which several analysis vessels are arranged centro-symmetrically. In this way, the lid of the analysis vessel acts on a piston that—depending on the internal pressure in the analysis vessel—is pressed into a hydraulic cylinder that is arranged in the upper flange. The hydraulic cylinder is connected to the measurement device by means of a hydraulic line, whereby the measurement device is arranged in the center of the upper flange. The hydraulic cylinder for the piston can also be arranged in the cap of the analysis vessel.

Using the attached drawing, various forms of embodiment of the device in accordance with the invention are elucidated in more detail, by way of example, in the following sections.

BRIEF DESCRIPTION OF THE DRAWINGS

The following aspects are shown in this connection.

DESCRIPTION OF THE PREFERRED EMBODIMENTS

Figure 1:
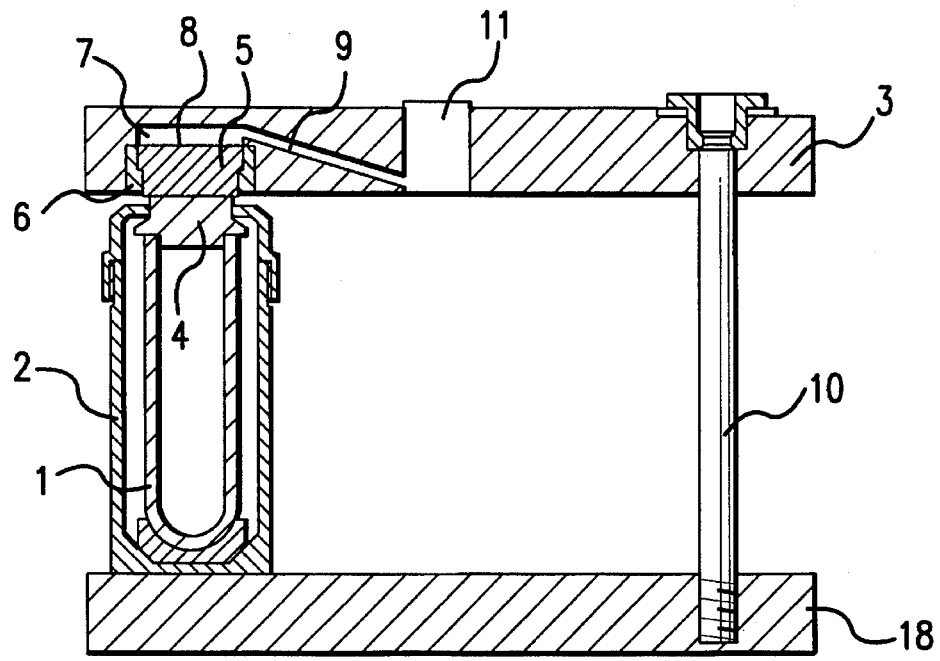
FIG. 1 shows a section through a form of embodiment of the device in accordance with the invention along the line A–B in FIG. 2.

FIG. 1 shows an analysis vessel 1, that is surrounded by an outer container 2, with a cap 3. The internal pressure of the analysis vessel 1 acts on a lid 4 that presses against the piston 5 in the event of increasing internal pressure in the analysis vessel 1 with maintenance of its sealing action, whereby the piston is guided through a bolt insert 6 in the flange 3. A hydraulic cylinder 7 for the piston 5 is located above the lid 4, whereby the hydraulic cylinder 7 has been filled with a hydraulic liquid. The hydraulic cylinder 7 is separated from the piston 5 by means of an elastic membrane 8. The hydraulic cylinder 7 is connected to a pressure measurement device via a hydraulic line 9.

Figure 3:
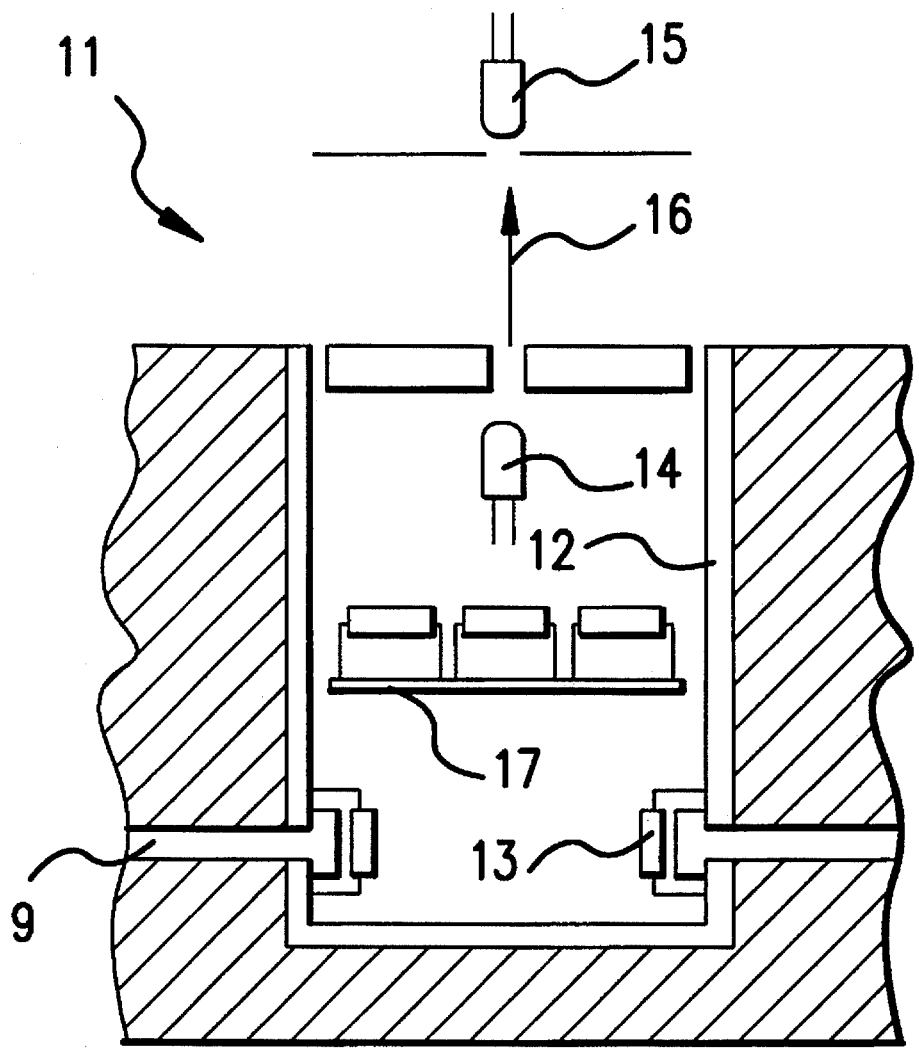
FIG. 3 shows a side view in sectional form through the measurement device.

An increase in the internal pressure in the analysis vessel 1 is therefore transferred to the hydraulic liquid in the hydraulic cylinder 7. In this way, a change in the internal pressure in the analysis vessel 1 is transferred to the measurement device 11 via the lid 4, the piston 5 and the hydraulic liquid. The device that is shown in FIG. 3 has been designed to monitor the pressure in six analysis vessels. Every analysis vessel 1 has a piston 5 assigned to it. The analysis vessels 1 that are arranged in the outer containers 2, the hydraulic system and the measurement device 11 form a complex unit. The centro-symmetrically arranged analysis vessels 1 are fixed between two flanges by means of bolt/nut connections 10. In this way, the hydraulic system has several arms 9 that extend radially outward toward the analysis vessels from a center in which the measurement device 11 has been arranged. One bolt/nut connection is advantageously provided per analysis vessel 1. In the center of the lower flange, means (not shown) are arranged for attaching the flange to a counter that is capable of rotation.

The measurement device 11, that is shown in FIG. 3, has a microwave-tight housing 12. Hydraulic lines 9 open out into the housing 12. Measurement recorders 13 transform the pressure values, that are obtained via a hydraulic liquid that is contained in the hydraulic lines 9, into electronic signals. Use can, for example, be made of piezoelectric pressure recorders as the measurement recorders. The electronic signals are transformed into light signals in a converter 17. The light signals are conveyed to a light receiver 15 via a light transmitter 14, whereby the light receiver is connected to a unit (not shown) for controlling the output of heat from the microwave oven.

Figure 2:
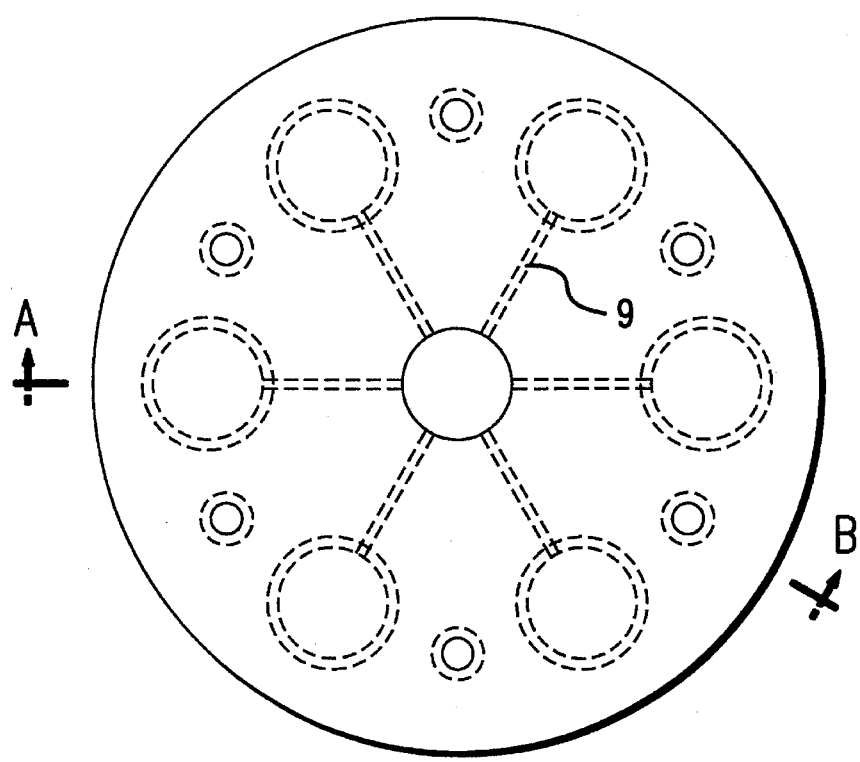
FIG. 2 shows a plan view in sectional form through the device that is shown in FIG. 1

The device that is shown in FIGS. 1 through 3 can also be used for measuring the temperature in the analysis vessels if a temperature measurement sensor, that is connected to the measurement device, is arranged, for example, in the lid of the analysis vessel or in the analysis vessel itself.

We claim:

1. A microwave oven for decomposition of chemical substances, comprising:

a control unit for generating a microwave field, said control unit being positioned outside said microwave field;

at least one pressure-tight analysis vessel, sealed with a lid and being positioned in said microwave field of said microwave oven whereby heat is supplied to said analysis vessel;

measurement sensors on said analysis vessel;

a device for measuring pressure and temperature in said analysis vessel, said measuring device being in a microwave-tight housing inside said microwave field;

a first non-electrical line connecting said measurement sensors to said measurement device; and a second non-electrical line connecting said measurement device to said control unit.

2. The microwave oven in accordance with claim 1, characterized by the feature that a measurement recorder (13) is arranged in the microwave-tight housing and converts the measured signals from the measurement sensor into an electronic signal.

3. The microwave oven in accordance with claim 1, characterized by the feature that an energy source for the measurement device (11) is arranged in the microwave-tight housing (12).

4. The microwave oven in accordance with claim 1, characterized by the feature that the measurement device (11) is connected, via a non-electrical line, to an energy source outside of the closed microwave-tight housing (12).

5. The microwave oven in accordance with claim 1, characterized by the feature that an energy converter for the conversion of microwave energy into electrical energy has been arranged in the closed microwave-tight housing (12), whereby a microwave-permeable zone has been provided in the housing (12).

6. The microwave oven in accordance with claim 1, characterized by the feature that a generator has been arranged in the closed microwave-tight housing (12), whereby the generator is driven mechanically from outside the housing (12).

7. The microwave oven in accordance with claim 1, characterized by the feature that a transmitter (14) for light has been arranged in the measurement device (11), whereby the transmitter for light serves in transferring the measurements to a receiver (15) that is arranged outside of the microwave oven and whereby the receiver is connected to the unit for controlling the heating apparatus.

8. The microwave oven in accordance with claim 7, characterized by the feature that the transmitter (14) and the receiver (15) are connected via a light conductor.

9. The microwave oven in accordance with claim 1, characterized by the feature that the measurement device (11) is connected, via a hydraulic line, to the control unit for the microwave oven.

10. The microwave oven in accordance with claim 1, characterized by the feature that the measurement sensors, that are arranged on the analysis vessel (1), are connected hydraulically, optically or thermally to the measurement device (11).

11. The microwave oven in accordance with claim 1, characterized by the feature that the device comprises an upper flange and a lower flange (3, 18) that are held together by centro-symmetrically arranged bolt/nut connections (10) and between which several analysis vessels (1) are arranged centro-symmetrically, that the lid (4) of the analysis vessel (1) acts on a piston (5), whereby a hydraulic cylinder (7) for the piston (5) has been arranged in the upper flange (3) and whereby the piston is connected to the measurement device (11) via a hydraulic line (9) and whereby the measurement device is arranged in the center of the upper flange (3).

* * * * *